United States Patent [19]
Tjoeng et al.

[11] Patent Number: 5,837,698
[45] Date of Patent: Nov. 17, 1998

[54] STEROID NITRITE AND NITRATE ESTER DERIVATIVES USEFUL AS ANTI-INFLAMMATORY DRUGS

[75] Inventors: Foe S. Tjoeng, Manchester; Mark G. Currie, St. Charles, both of Mo.; Mark E. Zupec, O'Fallon, Ill.

[73] Assignee: G. D. Searle & Co., Chicago, Ill.

[21] Appl. No.: 643,018

[22] Filed: May 2, 1996

[51] Int. Cl.⁶ .......................... A61K 31/57; A61K 31/58; C07J 17/00; C07J 71/00
[52] U.S. Cl. .......................... 514/169; 514/172; 514/174; 514/177; 514/178; 514/179; 514/180; 514/181; 514/182; 540/63; 540/67; 540/69; 540/70; 540/114
[58] Field of Search ................... 540/63, 64, 69, 540/70, 67, 114; 514/461, 463, 172, 174, 169, 177, 178, 179, 180, 181, 182

[56] References Cited

U.S. PATENT DOCUMENTS

| | | | |
|---|---|---|---|
| 2,990,401 | 6/1961 | Bernstein et al. | 260/239.55 |
| 3,002,010 | 9/1961 | Origoni et al. | 260/397.45 |
| 3,183,252 | 5/1965 | Crebbe | 260/397.4 |
| 3,215,713 | 11/1965 | Barton | 260/397.4 |
| 3,298,941 | 1/1967 | Barton | 204/158 |
| 3,639,434 | 2/1972 | Oxley et al. | 260/397.45 |
| 3,743,741 | 7/1973 | Laurent et al. | 424/242 |
| 3,839,369 | 10/1974 | Hofmeister et al. | 260/397.45 |
| 3,910,881 | 10/1975 | Scheller et al. | 260/210.5 |
| 3,930,970 | 1/1976 | Barton | 204/158 R |
| 5,416,205 | 5/1995 | Dlla Valle et al. | 514/54 |

FOREIGN PATENT DOCUMENTS

| | | |
|---|---|---|
| 969927 | 6/1975 | Canada . |
| 975755 | 10/1975 | Canada . |
| 2222491 | 5/1972 | Germany . |
| 1643034 | 8/1976 | Germany . |
| 4223800A1 | 1/1994 | Germany . |
| 1510131 | 2/1991 | U.S.S.R. . |
| 1082573 | 9/1967 | United Kingdom . |
| 1082574 | 9/1967 | United Kingdom . |
| WO9409771 | 5/1994 | WIPO . |
| WO9403421-A2 | 2/1997 | WIPO . |

OTHER PUBLICATIONS

Moncada et al; *Biochem.Pharm.* 38:1709–1715 (1989).
Moncada et al.; *Pharm.Review* 43:109–147 (1991).
Moncada et al.; *Jour.Cardio.Pharm.* 17:525 (1991).
Persson et al., *Eur.Jour.Pharm.* 249 R7–R8 (1993).
Alspaugh & Granger, *Infection and Immunity,* 59:2291–2296 (1991).
Wallace et al., *Eur.Jour.Pharm.* 257:249–255 (1994).
MacIntyre et al., *Proc.Nat.Acad.Sci.* USA 88 2936–2940 (1991).
Pipili–Synetos et al, *British Journal of Pharmacology,* 116, 1829–1834 (1995).
Leitold et al., *Arzneimittel Forschung Drug Research,* vol. 37, No. 6 (1987), 692–698.
Hayashi et al., *Chemical and Pharm. Bulletin,* vol. 41, No. 6 (1993), 1100–1110.
Bayunova et al., *Chem. Pharm. Journal,* vol. 14, No. 12 (1980), 60–62.
Miki et al., *Chemical Abstracts,* vol. 70, No. 9 (Mar. 3, 1969), Abstract No. 38001, p. 380, col. 2.
Campbell et al., "Infarct size reduction: review of the clinical trials". J Clinical Pharm vol. 26, 317–329, 1986.

*Primary Examiner*—Allen J. Robinson
*Assistant Examiner*—Barbara Badio
*Attorney, Agent, or Firm*—Dennis A. Bennett; Alan L. Scrivner

[57] ABSTRACT

The present invention relates to a pharmaceutical composition or preparation which comprises hydroxyl containing steroidal hormones and organic nitrite/nitrate or other nitric oxide donating agents.

11 Claims, No Drawings

STEROID NITRITE AND NITRATE ESTER DERIVATIVES USEFUL AS ANTI-INFLAMMATORY DRUGS

BACKGROUND OF THE INVENTION

1. Field of the Invention

The present invention relates to novel steroid nitrite/nitrate ester derivatives, and to their use treating inflammatory diseases.

2. Related Art

Steroids, specifically of the glucocorticoid class of molecules, are known to possess anti-inflammatory and immunomodulatory activities and are commonly utilized for the treatment of numerous autoimmune and inflammatory diseases. However, their beneficial effects are often slow to develop and accompanied by many dose-limiting side-effects. Nitric oxide donors, such as nitroglycerin, have also been utilized as pharmaceutical agents with prominent beneficial effects on the cardiovascular system. Many of the biological actions of nitric oxide potentially counteract the side-effects of the glucocorticoids and may enhance their therapeutic actions. The present invention relates to novel steroid nitrite/nitrate ester derivatives that possess the combined biological properties of glucocorticoids and nitric oxide donors in a single molecule. These molecules have an advantage over currently utilized glucocorticoids in that they rapidly elicit beneficial pharmacological effects, such as bronchial relaxation, through the release of nitric oxide. It is intended that these novel molecules be utilized for therapy, in particular their use as anti-inflammatory and immunosuppressive drugs for the treatment of rheumatic diseases, immunological disorders, skin disorders, inflammation, transplant rejection, cancer, osteoporosis, rhinitis and asthma with less side-effects.

Glucocorticoids are commonly utilized for the pharmacologic treatment of inflammation and undesirable immune system reactions. These steroids have the capacity to prevent or suppress the development of inflammation resulting from a number of different injurious agents including infectious, immunological, chemical, mechanical, and radiation. Glucocorticoids are also effective in the treatment of immune system disorders including autoimmune diseases such as rheumatoid arthritis and lupus, and transplant rejection. However, the therapeutic applications of these steroids are somewhat limited due to toxicity and side-effects. The major side effects of the glucocorticoids are hypertension, peptic ulcers, increased susceptibility to infections, osteoporosis, hyperglycemia, and vascular occlusion.

It has been known since the early 1980's that the vascular relaxation brought about by acetylcholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite ester, glyceryltrinitrate and other nitrovasodilators. The recent identification of EDRF as NO has coincided with the discovery of a biochemical pathway by which NO is synthesized from the amino acid L-arginine by the enzyme nitric oxide synthase. The NO released by the constitutive enzyme acts as a transduction mechanism underlying several physiological responses. The NO produced by the inducible enzyme is a cytotoxic molecule for tumor cells and invading microorganisms.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacology*, 38, 1709–1715 (1989) and Moncada et al, *Pharmacological Reviews*, 43, 109–142 (1991). Furthermore, NO has been shown to possess anti-thrombotic (see Moncada et al. *Journal of Cardiovascular Pharmacology* 17, S25 (1991), Bvrne et al., World Patent application W09403421-A2 and Schonafinger et al., German Patent application DE4223800-A1), bronchorelaxant (Persson et al. *European Journal of Pharmacology*, 249, R7–R8 (1993), anti inflammatory, microbialcidal (Alspaugh and Granger, *Infection and Immunity* 59, 2291–2296 (1991) and gastroprotective (see Wallace et al. *European Journal of Pharmacology*, 257, 249–255 (1994) effects in animal models. In addition, nitric oxide has been suggested to be effective against the loss of bone in in vitro models of osteoporosis (MacIntyre et al. *Proc. Natl. Acad. Sci. USA* 88, 2936–2940 (1991) and in inhibiting angiogenesis, tumour growth and metastasis in in vivo animal models (Pipili-Synetos et al. *British Journal of Pharmacology*, 116, 1829–1834 (1995). In U.S. Pat. Nos. 3,930,970, 3,298,941 and 3,215,713, a novel photochemical process for the preparation of diol mononitrates from alcohol nitrites is disclosed. In U.S. Pat. Nos. 3,639,434, 3,743,741 and 3,839,369, the preparation of steroid nitrate esters and their uses as intermediates is disclosed. In German Patent 1643034, a method for the preparation of steroid nitrate esters is disclosed. In Canadian Patent 975755 and 969927, a process for the preparation and acidolysis of nitrate esters of 21-alcohols of the pregnane series is disclosed, respectively. In British Patent 1,082,573 and 1,082,574, a process for the preparation of steroid-11-nitrate esters and their uses as intermediates is disclosed.

Thus, these properties make nitric oxide an ideal agent to enhance the actions of corticosteroids in the treatment of various diseases mentioned earlier by both increasing their biological effects as well as by reducing their side effects. The present invention relates to novel nitrite/nitrate esters of steroids, processes for their preparation, pharmaceutical compositions containing them, and methods for their use.

SUMMARY OF THE INVENTION

The present invention relates to a pharmaceutical composition or preparation which comprises hydroxyl containing steroidal hormones and organic nitrite/nitrate or other nitric oxide donating agents which can be administered simultaneously, sequentially or separately. Representative examples of hydroxyl containing steroidal hormones known in the art include those listed in the Merck Index, Eleventh Edition (1989) as follows (the respective compound numbers are given each):

| | |
|---|---|
| 21-Acetoxypregnenolone, 70 | Hydrocortisone Phosphate, 4712 |
| Alclometasone, 213 | Hydrocortisone 21-Sodium Succinate, 4713 |
| Algestone, 229 | |
| Amcinonide, 398 | Hydrocortisone terbutate, 4714 |
| Beclomethasone, 1029 | Mazipredone, 5644 |
| Betamethasone, 1202 | Medrysone, 5679 |
| Budesonide, 1455 | Meprednisone, 5750 |
| Chlorprednisone, 2157 | Methylprednisolone, 6028 |
| Clobetasol, 2361 | Mometasone Furoate, 6151 |
| Clocortolone, 2368 | Paramethasone, 6977 |
| Cloprednol, 2396 | Prednicarbate, 7177 |

-continued

| | |
|---|---|
| Corticosterone, 2532 | Prednisolone 21-Diethylaminoacetate, 7720 |
| Cortisone, 2533 | |
| Corticazol, 2536 | Prednisolone Sodium Succinate, 7722 |
| Deflazacort, 2852 | Prednisolone Sodium Phosphate, 7721 |
| Desonide, 2908 | Prednisplone Sodium 21-m-Sulfo-benzoate, 7723 |
| Dexamethasone, 2922 | Prednisolone 21-Stearoylglycolate, 7724 |
| Diflorasone, 3126 | |
| Diflucortolone, 3129 | Prednisolone Terbutate, 7725 |
| Difluprednate, 3134 | Prednisolone 21-Trimethylacetate, 7726 |
| Enoxolone, 3543 | |
| Fluazacort, 4048 | Prednisone, 7727 |
| Flucloronide, 4053 | Prednival, 7728 |
| Flumethasone, 4066 | Prednylidene, 7729 |
| Flunisolide, 4071 | Prednylidene 21-Diethylaminoacetate, 7730 |
| Flucinolone Acetonide, 4076 | |
| Fluocinonide, 4077 | Tixocortol, 9408 |
| Fluocortin Butyl, 4078 | Triamcinolone, 9511 |
| Fluocortolone, 4079 | Triamcinolone Acetonide, 9512 |
| Fluorometholone, 4104 | Triamcinolone Benetonide, 9513 |
| Fluperolone, Acetate, 4118 | Triamcinolone Hexacetonide, 9514 |
| Fluprednidene Acetate, 4115 | |
| Fluprednisolone, 4119 | |
| Flurandrenolide, 4112 | |
| Formocortal, 4156 | |
| Halcinonide, 4504 | |
| Halometasone, 4510 | |
| Haloprednone Acetate, 4512 | |
| Hydrocortamate, 4709 | |
| Hydrocortisone, 4710 | |

Not listed in the Merck Index
Fluticasone

Preferred examples are glucocorticoids and synthetic steroidal compounds with glucocorticoid activity. Representative examples of organic nitrites and nitrates or other nitric oxide donating compounds including such as glyceryl nitrate, amylnitrite, isosorbide mononitrate, isosorbide dinitrate, mannitol nitrate, pentaerythritol nitrate, propatyl nitrate and furoxan derivatives;

The present invention further discloses a preferred compound of Formula 1 and pharmaceutically acceptable ester and prodrugs thereof,

A—B—C                                    1 wherein;
A is a residue of a hydroxyl containing steroidal hormone. Representative examples of hydroxyl containing steroidal hormones known in the art include those listed in the Merck Index, Eleventh Edition (1989) as listed above. Preferred examples are glucocorticoids and synthetic steroidal compounds with glucocorticoid activity.

B is a spacer preferably containing a maximum of 12 carbon atoms, connecting A through the hydroxyl moeity and C through an amino or a hydroxyl group via an amide, ester, carbamate or carbonate linkage.

C is an organic nitrite or nitrate compound, or other nitric oxide donating compounds such as furoxan derivatives. Representative examples of organic nitrite or nitrate compounds are glyceryl nitrate, amylnitrite, isosorbide mononitrate, isosorbide dinitrate, mannitol nitrate, pentaerythritol nitrate, propatyl nitrate.

The scope of the compounds of the present invention is defined above by the Formula A—B—C (I) and preferably includes those characterized by the structural formula II and III, and pharmaceutically acceptable ester and prodrugs thereof,

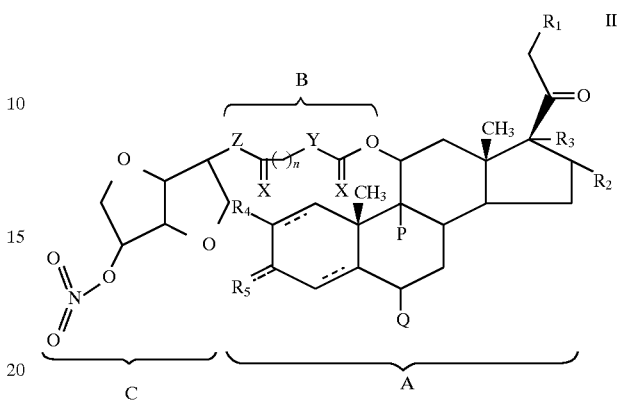

wherein;
the dotted lines in Formula II indicate a single or a double bond;

$R_1$ is selected from the group consisting of hydrogen, hydroxyl, nitrite ester (ONO), nitrate ester ($ONO_2$) halogen, thiol, alkylmercapto, heterocycles, lower alkoxy, alkylsilyloxy, lower alkyl, wherein all said radicals may optionally be substituted with hydroxy, lower alkyl, lower alkenyl, lower alkynyl, lower alkoxy, amino, nitro, nitrile, carboxyl and haloalkyl radicals; or $R_1$ is a group of the formula OCO—$R_6$ wherein $R_6$ is alkanoic acid, lower alkyl, lower alkenyl, lower alkynyl, or lower alkoxy group;

$R_2$ and $R_3$ are independently selected from the group consisting of hydrogen, hydroxyl, nitrite ester (ONO), nitrate ester ($ONO_2$), lower alkyl, lower alkenyl, lower alkynyl, lower alkoxy wherein all said radicals may optionally be substituted with hydroxy, lower alkyl, lower alkenyl, lower alkynyl, lower alkoxy, amino, nitro, nitril, carboxyl and haloalkyl radicals;or $R_2$ and $R_3$ are independently selected from the group of formula OCO—$R_7$ wherein $R_7$ is 2-furanyl, lower alkyl or lower alkoxy group, $R_2$ and $R_3$ may optionally form a cyclic structure of the formula:

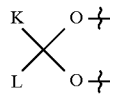

wherein, K and L are selected from the group consisting of hydrogen, and lower alkyl, or optionally K and L can form an alicyclic hydrocarbon ring or heterocyclic ring;

$R_4$ is hydrogen or halogen;

$R_5$ is hydrogen, hydroxyl or oxygen;

P and Q are independently selected from the group consisting of hydrogen, chloro, fluoro and lower alkyl group;

X is oxygen or sulfur;

Y is methylene, oxygen or amino;

Z is oxygen or amino group; and n is about 1 to 4.

In a preferred embodiment of the above mentioned compound the following are preferred;

R₁ is selected from the group consisting of hydrogen, hydroxyl, nitrite ester (ONO), nitrate ester (ONO₂), halogen, thiol, alkylmercapto group of 1 to about 6 carbon atoms, heterocyclic group of 2 to 5 carbon atoms and 1 to 2 hetero atoms, lower alkoxy group of 1 to about 6 carbon atoms, alkylsilyloxy group of 3 to about 8 carbon atoms, lower alkyl group of 1 to about 6 carbon atoms, wherein all said radicals may optionally be substituted with hydroxy, lower alkyl, lower alkenyl, lower alkynyl, lower alkoxy, amino, nitro, nitrite, carboxyl and haloalkyl radicals; or R₁ is a group of the formula OCO—R₆ wherein R₆ is alkanoic acid group of 2 to about 6 carbon atoms, lower alkyl group of 1 to about 6 carbon atoms, lower alkenyl group of 2 to about 6 carbon atoms, lower alkynyl group of 2 to about 6 carbon atoms, or lower alkoxy group of 1 to about 6 carbon atoms;

R₂ and R₃ are independently selected from the group consisting of hydrogen, hydroxyl, nitrite ester (ONO), nitrate ester (ONO₂) lower alkyl group of 1 to about 6 carbon atoms, lower alkenyl group of 2 to about 6 carbon atoms, lower alkynyl group of 2 to about 6 carbon atoms, lower alkoxy group of 1 to about 6 carbon atoms, wherein all said radicals may optionally be substituted with hydroxy, lower alkyl, lower alkenyl, lower alkynyl, lower alkoxy, amino, nitro, nitril, carboxyl and haloalkyl radicals; or R₂ and R₃ are a group of formula OCO—R₇, wherein R₇ is 2-furanyl, lower alkyl group of 1 to about 6 carbon atoms or lower alkoxy group of 1 to about 6 carbon atoms;

R₂ and R₃ may optionally form a cyclic structure of the formula:

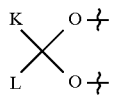

wherein, K and L are selected from the group consisting of hydrogen, and lower alkyl group of 1 to about 6 carbon atoms; optionally K and L can form an alicyclic hydrocarbon ring preferably containing a maximum of 8 carbon atoms or a heterocyclic ring preferably containing a maximum of 6 carbon atoms and 2 heteroatoms selected from nitrogen, oxygen or sulfur;

P and Q are independently selected from the group consisting of hydrogen, chloro, fluoro and lower alkyl group of 1 to about 6 carbon atoms.

The rest being as defined above.

Another embodiment is;

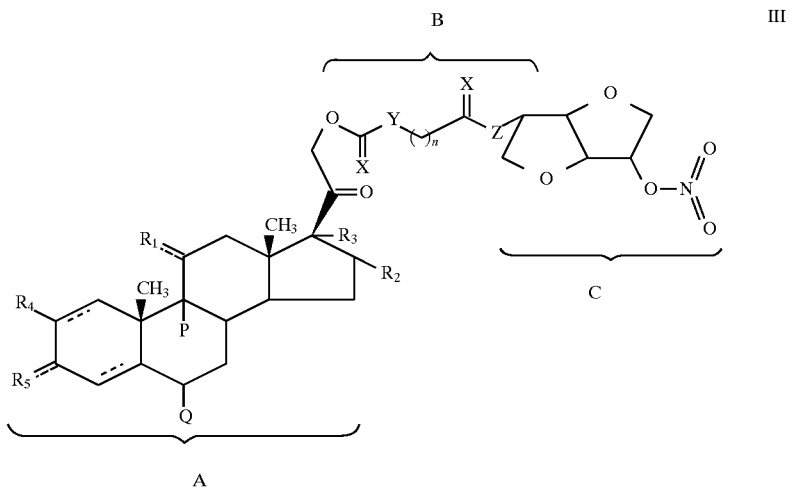

and wherein;

the dotted line in Formula III indicates a single or a double bond;

R₁ is selected from the group consisting of hydrogen, hydroxyl, nitrite ester (ONO), nitrate ester (ONO₂) oxygen (ketone), lower alkoxy, alkylsilyloxy, lower alkyl, wherein all said radicals may optionally be substituted with hydroxy, lower alkyl, lower alkenyl, lower alkynyl, lower alkoxy, amino, nitro and haloalkyl radicals; or R₁ is selected from the group of the formula OCO—R₆ wherein R₆ is alkanoic acid, lower alkyl, lower alkenyl, lower alkynyl or lower alkoxy group;

R₂ and R₃ are independently selected from the group consisting of hydrogen, hydroxyl, nitrite ester (ONO), nitrate ester (ONO₂), lower alkyl, lower alkenyl, lower alkynyl, lower alkoxy, wherein all said radicals may optionally be substituted with hydroxy, lower alkyl, lower alkenyl, lower alkynyl, lower alkoxy, amino, nitro, nitrile, carboxyl and haloalkyl radicals; or R₂ and R₃ are independently selected from the group of the formula OCO—R₇ wherein R₇ is 2-furanyl, lower alkyl, lower alkenyl, lower alkynyl or lower alkoxy group; or R₂ and R₃ may optionally form a cyclic structure of the formula:

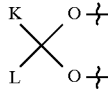

wherein, K and L are selected from the group consisting of hydrogen, and lower alkyl; or optionally K and L can form an alicyclic hydrocarbon or heterocyclic ring $R_4$ is hydrogen or halogen;

$R_5$ is hydrogen, hydroxyl or oxygen

P and Q are independently selected from the group consisting of hydrogen, chloro, fluoro and lower alkyl;

X is oxygen or sulfur;

Y is methylene, oxygen or amino;

Z is oxygen or amino; and n is about 1 to 4.

In a preferred embodiment of the above mentioned compound the following are preferred;

$R_1$ is selected from the group consisting of hydrogen, hydroxyl, nitrite ester (ONO), nitrate ester ($ONO_2$), halogen, thiol, alkylmercapto group of 1 to about 6 carbon atoms, heterocyclic group of 2 to 5 carbon atoms and 1 to 2 hetero atoms, lower alkoxy group of 1 to about 6 carbon atoms, alkylsilyloxy group of 3 to about 8 carbon atoms, lower alkyl group of 1 to about 6 carbon atoms, wherein all said radicals may optionally be substituted with hydroxy, lower alkyl, lower alkenyl, lower alkynyl, lower alkoxy, amino, nitro, nitrite, carboxyl and haloalkyl radicals; or $R_1$ is a group of the formula OCO—$R_6$ wherein $R_6$ is alkanoic acid group of 2 to about 6 carbon atoms, lower alkyl group of 1 to about 6 carbon atoms, lower alkenyl group of 2 to about 6 carbon atoms, lower alkynyl group of 2 to about 6 carbon atoms, or lower alkoxy group of 1 to about 6 carbon atoms;

$R_2$ and $R_3$ are independently selected from the group consisting of hydrogen, hydroxyl, nitrite ester (ONO), nitrate ester ($ONO_2$), lower alkyl group of 1 to about 6 carbon atoms, lower alkenyl group of 2 to about 6 carbon atoms, lower alkynyl group of 2 to about 6 carbon atoms, lower alkoxy group of 1 to about 6 carbon atoms, wherein all said radicals may optionally be substituted with hydroxy, lower alkyl, lower alkenyl, lower alkynyl, lower alkoxy, amino, nitro, nitril, carboxyl and haloalkyl radicals; or $R_2$ and $R_3$ are a group of formula OCO—$R_7$ wherein $R_7$ is 2-furanyl, lower alkyl group of 1 to about 6 carbon atoms or lower alkoxy group of 1 to about 6 carbon atoms;

$R_2$ and $R_3$ may optionally form a cyclic structure of the formula:

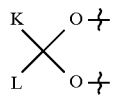

wherein, K and L are selected from the group consisting of hydrogen, and lower alkyl group of 1 to about 6 carbon atoms; optionally K and L can form an alicyclic hydrocarbon ring preferably containing a maximum of 8 carbon atoms or a heterocyclic ring preferably containing a maximum of 6 carbon atoms and 2 heteroatoms selected from nitrogen, oxygen or sulfur;

P and Q are independently selected from the group consisting of hydrogen, chloro, fluoro and lower alkyl group of 1 to about 6 carbon atoms.

The rest being as defined above.

While it may be possible for the preparations or compounds as defined above to be administered as the raw chemical, it is preferable to present them as a pharmaceutical formulation. According to a further aspect, the present invention provides a pharmaceutical formulation comprising a preparation or a compound as defined above or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a preparation or a compound as defined above or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers, or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Formulations for administration by inhalation can be prepared for use as an aerosolized medicaments such as in manner recited in U.S. Pat. No. 5,458,135 and U.S. Pat. No. 5,447,150.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.01 to 500 mg/kg per day. The dose range for adult humans is generally from 0.1 mg to 1 g/day. Tablets or other forms of presentation provided in discrete units may conveniently contain an amount of compound of the invention which is effective at such dosage or as a multiple of the same, for instance, units containing 0.05 mg to 250 mg, usually around 0.1 mg to 100 mg.

The compounds of formula (I) are preferably administered by inhalation, orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethyl-butyn-1-yl radicals and the like.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "alicyclic hydrocarbon" means an aliphatic radical in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "heterocyclic radical" means a saturated or unsaturated cyclic hydrocarbon radical with 4 to about 10 carbon atoms, preferably about 5 to about 6; wherein 1 to about 3 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazonlinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

The term "halogen" means fluorine, chlorine, bromine or iodine.

The term "prodrug" refers to a compound that is made more active in vivo.

As used herein, reference to "treatment" of a patient is intended to include prophylaxis.

All references, patents or applications, U.S. or foreign, cited in this application are hereby incorporated by reference as if written herein.

Starting materials used to make the present invention are commercially available such as from Sigma.

Four general synthetic schemes are outlined below for the compounds of the present invention.

SCHEME I
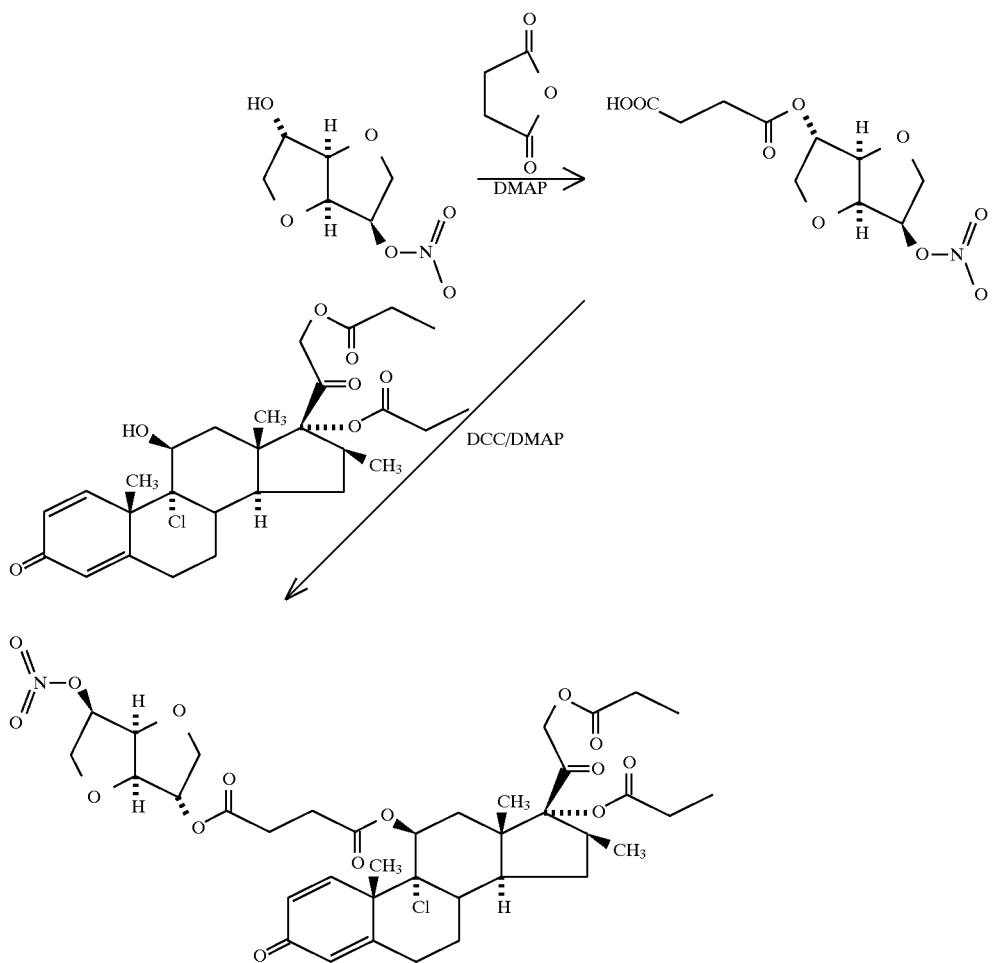
SCHEME II
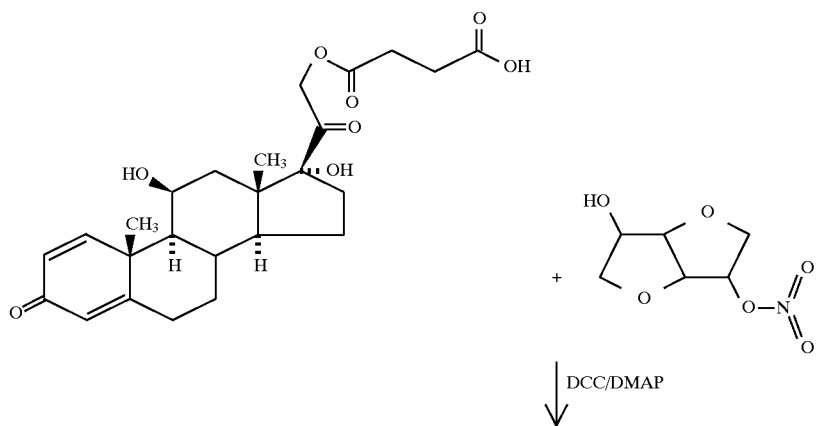

-continued
SCHEME II
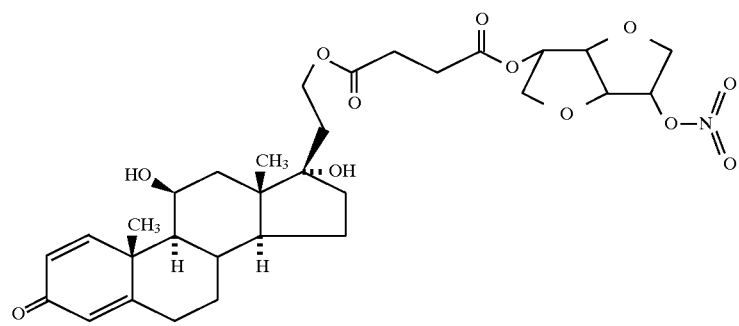
SCHEME III
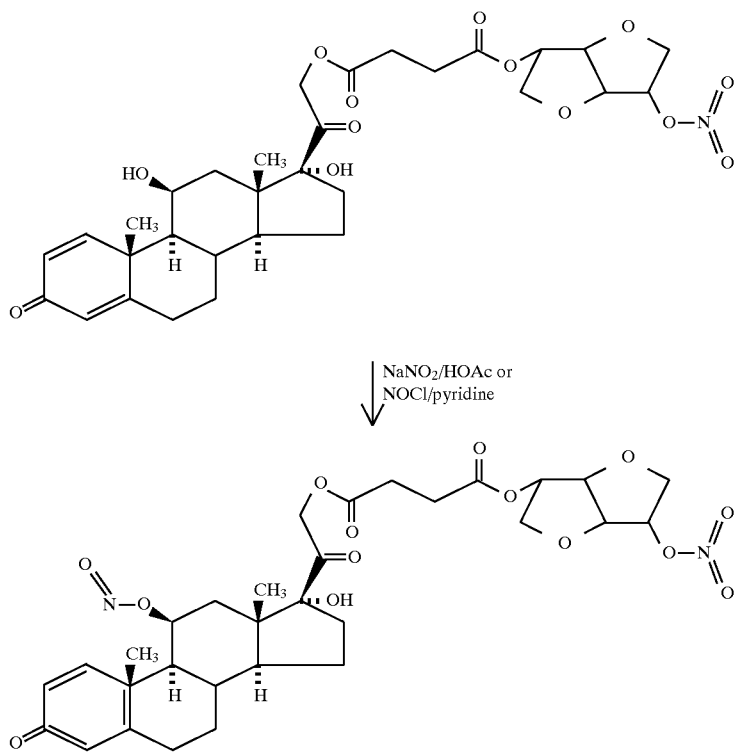

SCHEME IV

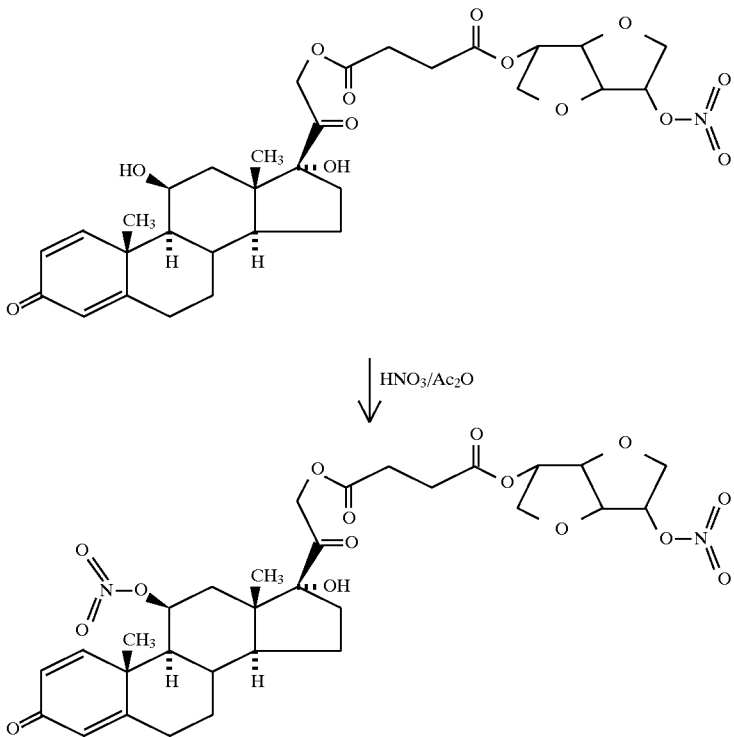

It will be obvious to one skilled in the art to make modifications in the choice of starting materials and process conditions to make all of the invention compounds disclosesd herein.

The invention is illustrated by the following examples.

EXAMPLE 1

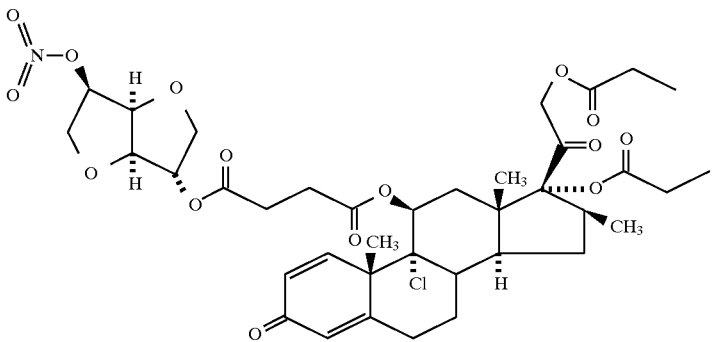

Isosorbide-5-nitrate (0.39 g; 2 mmoles) and 4-dimethylamino-pyridine (0.1 g) were added to a suspension of succinic anhydride (0.22 g; 2.2 mmoles) in dichloromethane (25 ml) with stirring. The clear reaction mixture was then stirred at room temperature overnight. 9α-chloro-16β-methylprednisolone-17, 21-dipropionate (1 g; 1.9 mmoles), dicyclohexylcarbodiimide (0.45 g; 2.2 mmoles) and 4-dimethylaminopyridine (0.1 g) in dichloromethane (100 ml) were added and the mixture was stirred for another day. The solid was filtered and the filtrate was taken down to dryness. The residue was purified on a Waters μBondapak column (30 cm×5 cm) using a linear gradient of 25–75% acetonitrile/water/trifluoroacetic acid. The desired fractions were collected and lyophylized to give 400 mg of white material. FAB-MS: $(M+Li)^+=800$; $^1$H-NMR (CDCl$_3$) δ 0.88 (s, 3H, CH$_3$(C-18)), 1.1–1.2 (m, 6H, 2CH$_3$—CH$_2$), 1.35 (d, 3H, CH—CH$_3$), 1.55 (s, 3H, CH$_3$(C-19)), 2.35–2.5 (m, 4H, 2CH$_3$—CH$_2$), 2.51–2.7 (m, 4H, CO—(CH$_2$)$_2$—CO), 3.85–4.05 (m, 4H, isosorbide), 4.25 and 4.7 (2d, 2H, CO—CH$_2$—O), 4.5 (m, 1H, isosorbide), 4.98 (m, 1H, isosorbide), 5.38 (d, 1H, CH(C-11)), 5.62 (m, 1H, isosorbide), (6.1 (s, 1H, CH(C-4)), 6.35 (d, 1H, CH(C-2)), 6.85 (d, 1H, CH(C-1)).

EXAMPLE 2
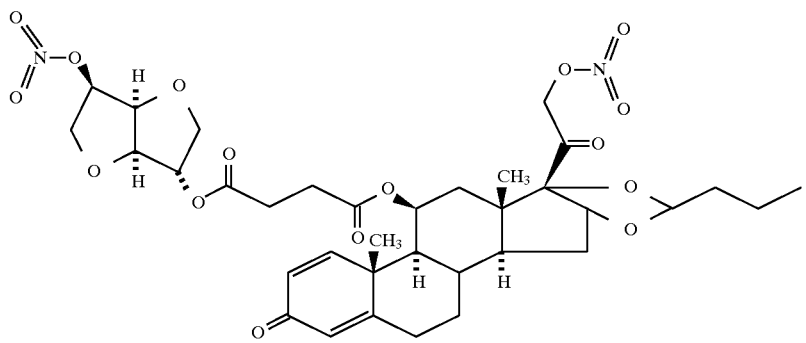
The title compound is prepared from budesonide-21-nitrate in the same manner as described for EXAMPLE 1.
EXAMPLE 3
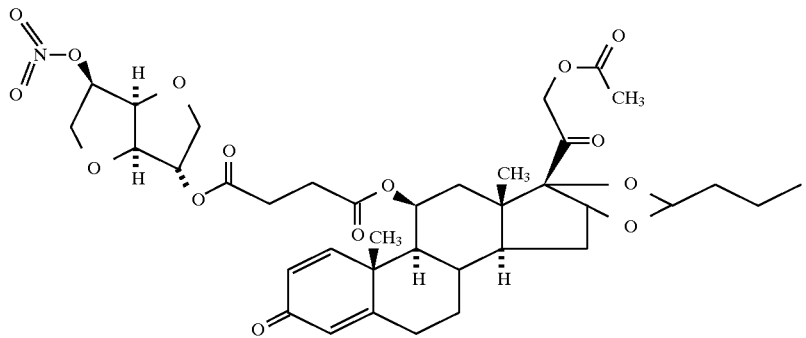
The title compound is prepared from budesonide-21-acetate in the same manner as described for EXAMPLE 1.
EXAMPLE 4
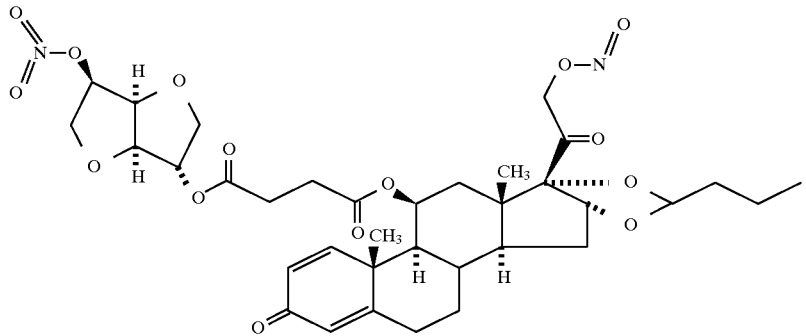
The title compound is prepared from budesonide-21-nitrite in the same manner as described for EXAMPLE 1.

EXAMPLE 5

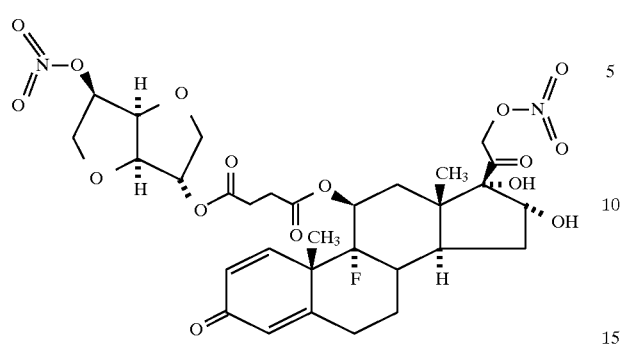

The title compound is prepared from triamcinolone-21-nitrate in the same manner as described for EXAMPLE 1.

EXAMPLE 6

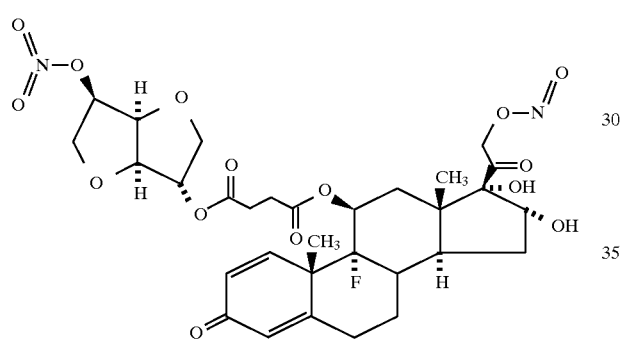

The title compound is prepared from triamcinolone-21-nitrite in the same manner as described for EXAMPLE 1.

EXAMPLE 7

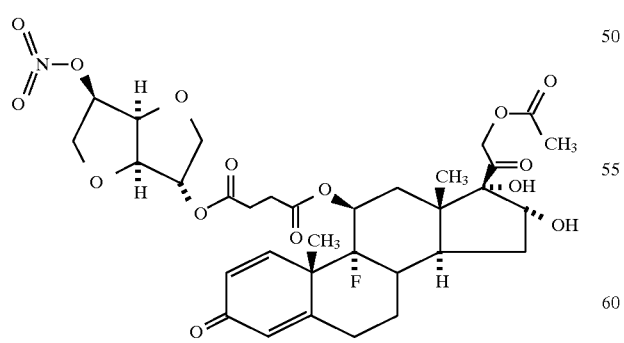

The title compound is prepared from triamcinolone-21-acetate in the same manner as described for EXAMPLE 1.

EXAMPLE 8

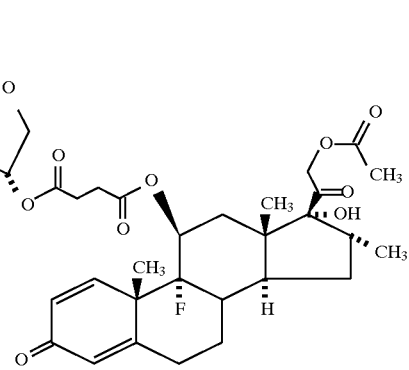

The title compound is prepared from dexamethasone-21-acetate in the same manner as described for EXAMPLE 1.

EXAMPLE 9

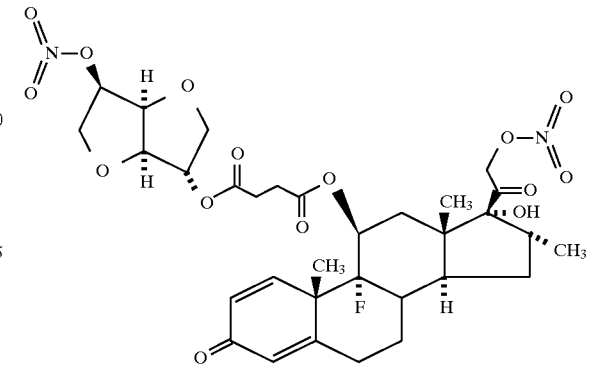

The title compound is prepared from dexamethasone-21-nitrate in the same manner as described for EXAMPLE 1.

EXAMPLE 10

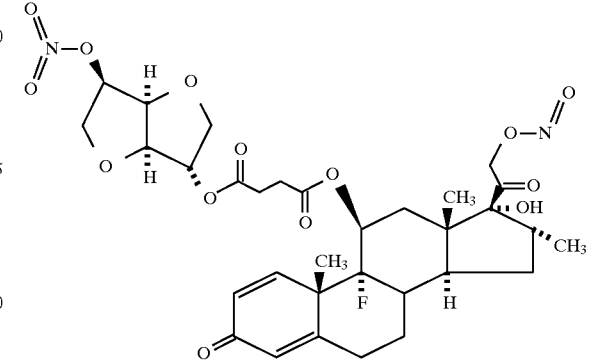

The title compound is prepared from dexamethasone-21-nitrite in the same manner as described for EXAMPLE 1.

EXAMPLE 11
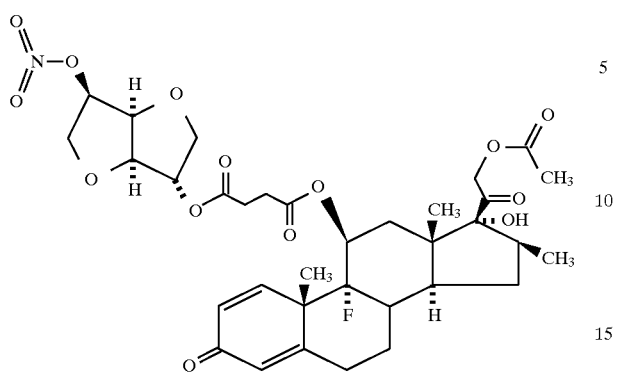
The title compound is prepared from betamethasone-21-acetate in the same manner as described for EXAMPLE 1.
EXAMPLE 12
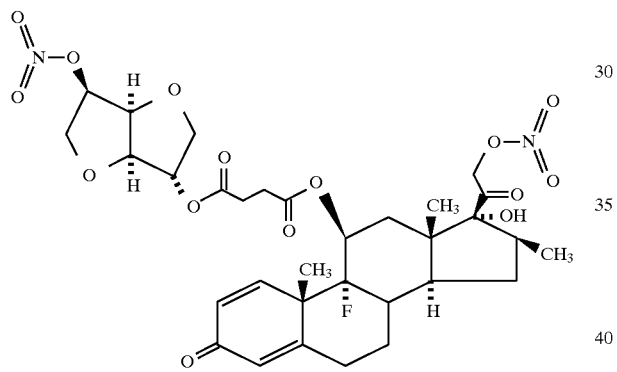
The title compound is prepared from betamethasone-21-nitrate in the same manner as described for EXAMPLE 1.
EXAMPLE 13
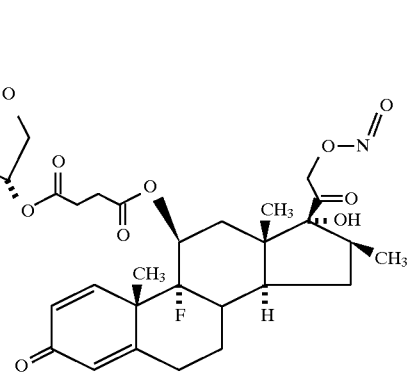
The title compound is prepared from betamethasone-21-nitrite in the same manner as described for EXAMPLE 1.
EXAMPLE 14
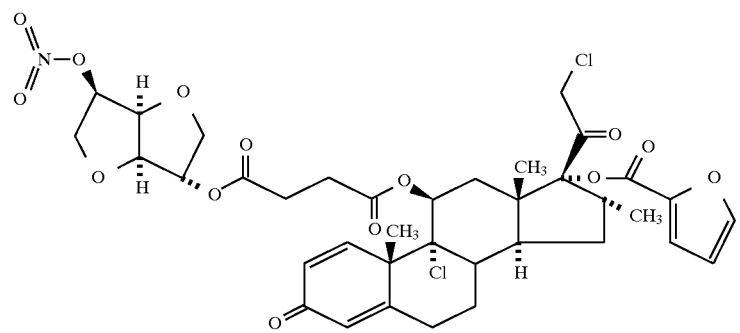

The title compound is prepared from mometasone furoate in the same manner as described for EXAMPLE 1.

EXAMPLE 15

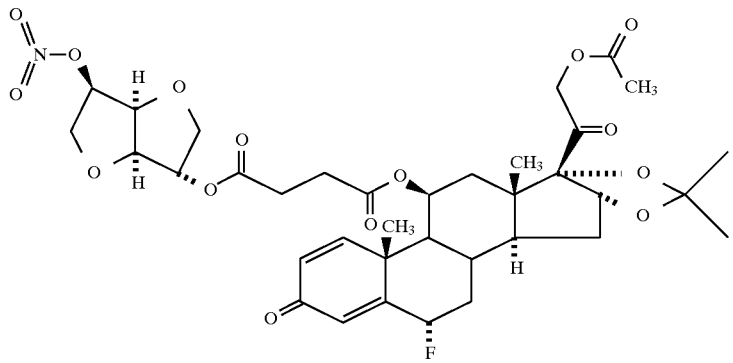

The title compound is prepared from flunisolide-21-acetate in the same manner as described for EXAMPLE 1.

EXAMPLE 16

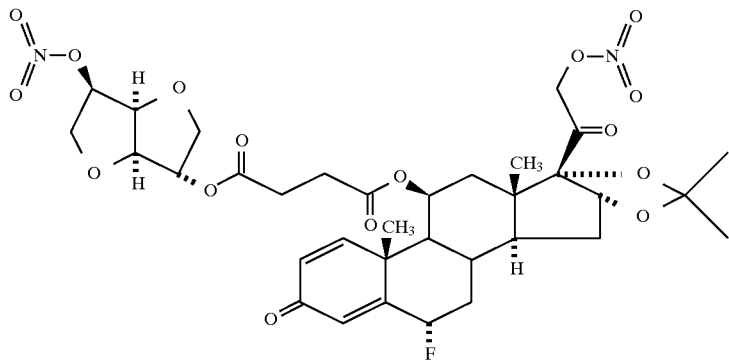

The title compound is prepared from flunisolide-21-nitrate in the same manner as described for EXAMPLE 1.

EXAMPLE 17

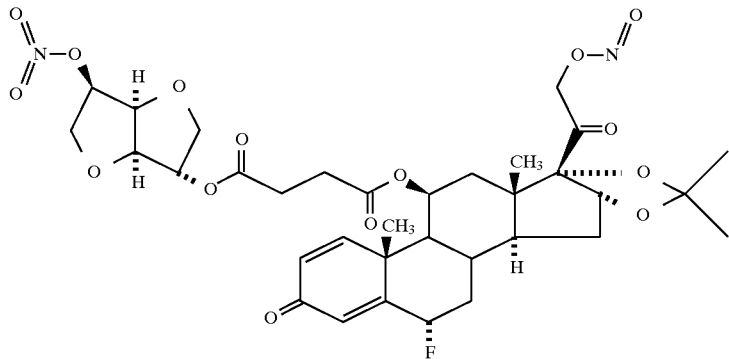

The title compound is prepared from flunisolide-21-nitrite in the same manner as described for EXAMPLE 1.

EXAMPLE 18

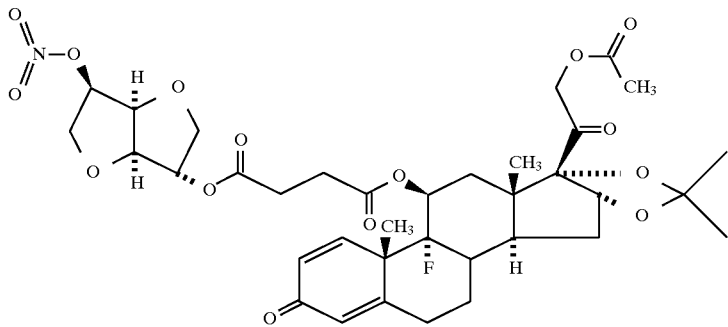

The title compound is prepared from triamcinolone-21-acetate acetonide in the same manner as described for EXAMPLE 1.

EXAMPLE 19

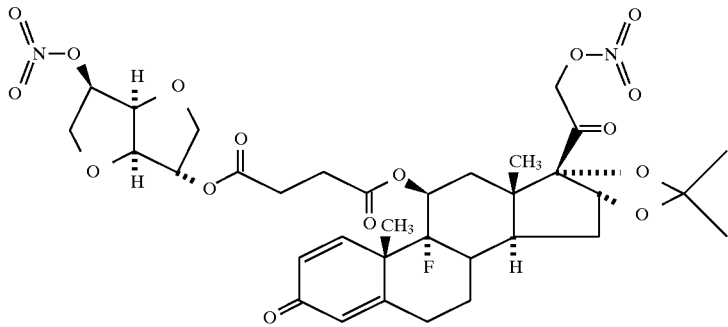

The title compound is prepared from triamcinolone-21-nitrate acetonide in the same manner as described for EXAMPLE 1.

EXAMPLE 20

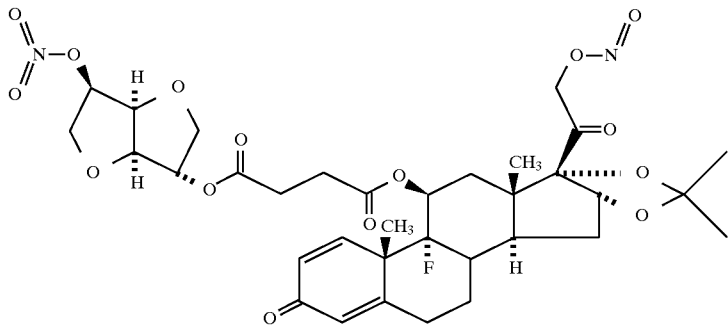

The title compound is prepared from triamcinolone-21-nitrite acetonide in the same manner as described for EXAMPLE 1.

EXAMPLE 21

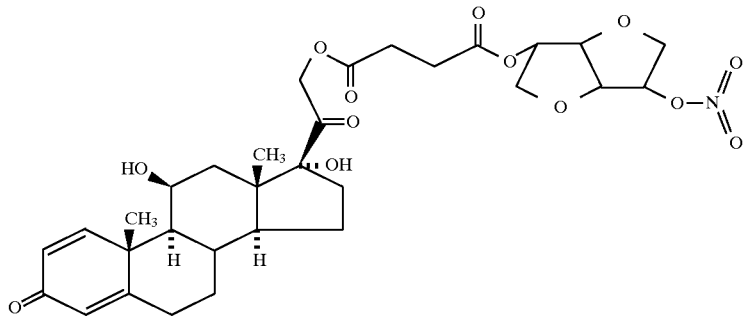

Prednisolone-21-hemisuccinate (0.47 g; 1 mmole), isosorbide-5-mononitrate (0.9 g; 5 mmoles) and DMAP (100 mg) were dissolved in chloroform (20 ml) and dimethylformamide (2 ml). To this solution, dicyclohexylcarbodiimide (0.26 g; 1.3 mmoles) in chloroform (5 ml) was added with stirring. The reaction mixture was stirred overnight and filtered. The filtrate was taken down to dryness and the residue was purified on a Waters μBondapak column (30 cm×5 cm) using a linear gradient of 25–75% acetonitrile/ water/ trifluoroacetic acid. The desired fractions were collected and lyophylized to give mg of white material. FAB-MS: $(M+Li)^+=640$; $^1$H-NMR (CDCl$_3$) δ 0.97 (s, 3H, CH$_3$ (C-18)), 1.47 (s, 3H, CH$_3$(C-19)), 2.6–2.85 (m, 4H, CO—(CH$_2$)$_2$—CO), 3.85–4.1 (m, 4H, isosorbide), 4.5 and 5.0 (m, 2H, isosorbide), 4.5 (d, 1H, CH(C-11)), 6.06 (s, 1H, CH(C-4)), 6.35 (d, 1H, CH(C-2)), 7.37 (d, 1H, CH(C-1)).

Fuming nitric acid (1 ml; d=1.49) and acetic anhydride (2.5 ml) are combined at −10° C. To this solution, a pre-cooled suspension of EXAMPLE 21 (1 mmole) in chloroform (20 ml) is added dropwise with stirring. The mixture is stirred for 4 h at 0° C. and poured into ice water (50 ml). The organic phase is separated and washed with water, saturated sodium bicarbonate solution and water. After drying over sodium sulfate overnight, the solid is filtered and the filtrate is taken down to dryness. The residue is purified on a Waters μBondapak column (30 cm×5 cm) using a linear gradient of 25–75% acetonitrile/water/trifluoroacetic acid.

EXAMPLE 22

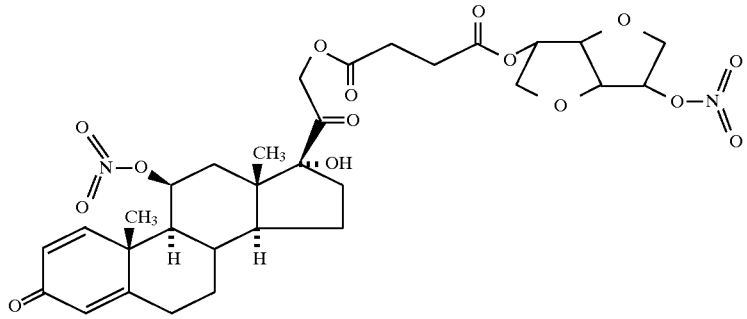

EXAMPLE 23

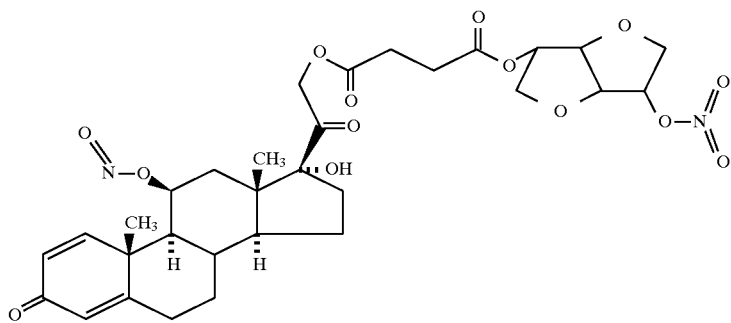

A solution of EXAMPLE 21 (0.02 mmoles) in acetic acid (1 ml) is warmed up to 55° C. and treated with solid sodium nitrite (0.007 g; 0.1 mmole) for 30 seconds. The product is precipitated by addition of ice water (5 ml) and filtered. The solid is washed with water and dried over $P_2O_5$ in vacuo to give a white solid material.

EXAMPLE 24

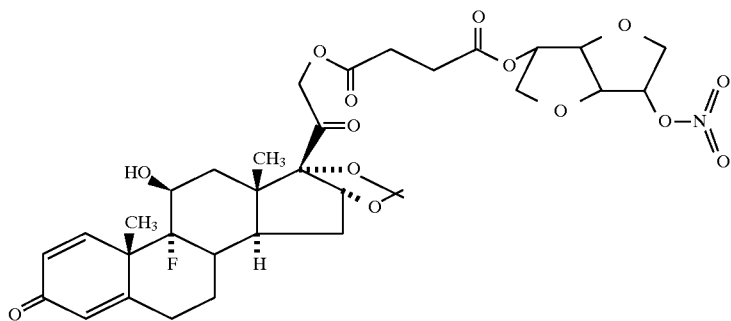

Triamcinolone-21-hemisuccinate acetonide (1 mmole), isosorbide-5-mononitrate (5 mmoles) and DMAP (100 mg) are dissolved in chloroform (20 ml) and dimethylformamide (2 ml). To this solution, dicyclohexylcarbodiimide (1.3 mmoles) in chloroform (5 ml) is added with stirring. The reaction mixture is stirred overnight and worked up as described tor EXAMPLE 21 to give the title compound.

EXAMPLE 25

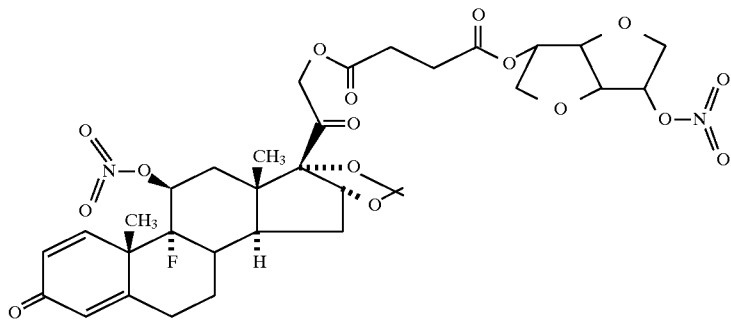

The title compound is prepared from EXAMPLE 24 in the same manner as described in the preparation of EXAMPLE 22.

EXAMPLE 26

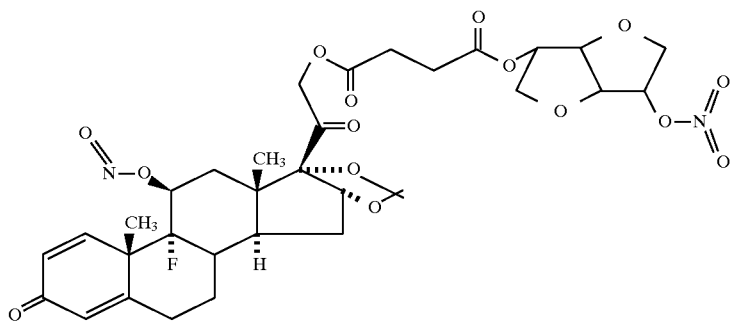

The title compound is prepared from EXAMPLE 24 in the same manner as described in the preparation of EXAMPLE 23.

Biological Data

The subject compounds have been found to be nitric oxide donors while maintaining their steroid activities and possess useful pharmacological properties as demonstrated by EXAMPLE 1 and EXAMPLE 21 in the in vitro smooth relaxant activity assay: The test compound and the parent steroid were examined for the ability to relax smooth muscle. The rat aortic ring assay was utilized as a bioassay to measure the relaxant activity. The rings were precontracted with phenylephrine (0.3 uM) and subsequently compounds were added to the tissue bath in the presence of cysteine (Cys) and $N^G$-L-nitroarginine methyl ester (L-NAME):

A. In vitro smooth muscle relaxant activity assay in the presence of Cys and L-NAME:

| Compound | Relaxation, $EC_{50}$ [uM] |
| --- | --- |
| Beclomethasone-dipropionate | 100 |
| Example 1 | >10 |
| Example 21 | 3 |

These data indicate that these compounds have smooth muscle relaxant activity, while the control compound Beclomethasone-dipropionate did not show any effect.

B. In vitro inhibiton of prostaglandin $E_2$ ($PGE_2$) synthesis assay: Human fetal fibroblast cells were treated with IL-1 for 16 hours and prostaglandin $E_2$ was measured by an ELISA. Compounds were given at the time of addition of IL-1. This assay provides an in vitro assessment of the compound to block the induction of the proinflammatory agent prostaglandin $E_2$ ($PGE_2$):

| Treatment | $PGE_2$ (ng) |
| --- | --- |
| Basal | 0.6 |
| IL-1 | 9.4 |
| IL-1 and Dexamethasone(10 uM) | 0.6 |
| IL-1 and Example 1(10 uM) | 0.5 |
| IL-1 and Example 21 (10 uM) | 0.4 |

These data indicate that the steroids with the modifications for the generation of nitric oxide are effective at inhibiting the increase in $PGE_2$ and maintain the glucocorticoid action of the prevention of prostaglandin formation.

What is claimed is:

1. A compound having the formula:

$$A—B—C \qquad 1$$

wherein;

A is a hydroxyl containing steroidal moiety;

C is an nitrite or nitrate containing moiety; and

B is a linking group comprising a lower alkyl, lower alkenyl, or lower alkynyl, wherein A is linked to C via the linking group B, and wherein the linking group B is attached to the hydroxyl of said A at the 11- or 21-position.

2. The compound as recited in claim 1 wherein;

A is selected from the group consisting of

| | |
| --- | --- |
| 21-Acetoxypregnenolone, | Hydrocortisone Phosphate, |
| Alclometasone, | Hydrocortisone 21-Sodium Succinate, |
| Algestone, | |
| Amcinonide, | Hydrocortisone terbutate, |
| Beclomethasone, | Mazipredone, |
| Betamethasone, | Medrysone, |
| Budesonide, | Meprednisone, |
| Chlorprednisone, | Methylprednisolone, |
| Clobetasol, | Mometasone Furoate, |
| Clocortolone, | Paramethasone, |
| Cloprednol, | Prednicarbate, |
| Corticosterone, | Prednisolone 21-Diethylaminoacetate, |
| Cortisone, | |
| Corticazol, | Prednisolone Sodium Phosphate, |
| Deflazacort, | Prednisoione Sodium Succinate, |
| Desonide, | Prednisolone Sodium 21-m-Sulfobenzoate, |
| Dexamethasone, | Prednisolone 21-Stearoylglycolate, |
| Diflorasone, | |
| Diflucortolone, | Prednisolone Terbutate, |
| Difluprednate, | Prednisolone 21-Trimethylacetate, |
| Enoxolone, | |
| Fluazacort, | Prednisone, |
| Flucloronide, | Prednival, |
| Flumethasone, | Prednylidene, |
| Flunisolide, | Prednylidene 21-Diethylaminoacetate, |
| Flucinolone Acetonide, | |
| Fluocinonide, | Tixocortol, |
| Fluocortin Butyl, | Triamcinolone |
| Fluocortolone, | Triamcinolene Acetonide, |
| Fluorometholone, | Triamcinolone Benetonide, |
| Fluperolone Acetate, | Triamcinolone Hexacetonide, |
| Fluprednidene Acetate, | |
| Fluprednisolone, | |
| Flurandrenolide, | |
| Formocortal, | |
| Halcinonide, | |
| Halometasone, | |
| Haloprednone Acetate, | |
| Hydrocortamate, | |

Hydrocortisone,
and
Fluticasone.

and
Fluticasone.

3. The compound as recited in claim 1 wherein C is glyceryl nitrate, amylnitrite, isosorbide mononitrate, isosorbide dinitrate, mannitol nitrate, pentaerythritol nitrate or propatyl nitrate.

4. A compound having the formula:

A—B—C    1 wherein;
A is a hydroxyl containing steroidal moiety;
C is an nitrite or nitrate containing moiety; and
B is a lower alkyl, lower alkenyl, or lower alkynyl, wherein B is attached to the hydroxyl of A at the 11- or 21-position and to C through an amino or a hydroxy group via an amide, ester, carbamate or carbonate linkage.

5. A compound having the formula:

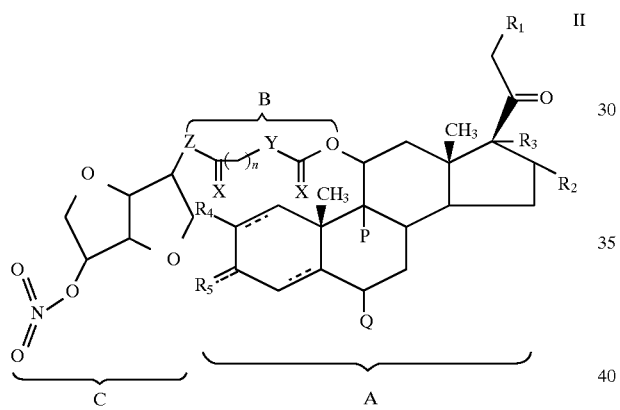

wherein;
the dotted lines in Formula II indicate a single or a double bond;
$R_1$ is selected from the group consisting of hydrogen, hydroxyl, nitrite ester (ONO), nitrate ester ($ONO_2$), halogen, thiol, alkylmercapto, heterocycles, lower alkoxy, alkylsilyloxy, lower alkyl, wherein each of said radicals may optionally be substituted with a hydroxy, lower alkyl, lower alkenyl, lower alkynyl, lower alkoxy, amino, nitro, nitrile, carboxyl or haloalkyl radical; or
$R_1$ is of formula OCO—$R_6$ wherein $R_6$ is an alkanoic acid, lower alkyl, lower alkenyl, lower alkynyl, or lower alkoxy group;
$R_2$ and $R_3$ are independently selected from the group consisting of hydrogen, hydroxyl, nitrite ester (ONO), nitrate ester ($ONO_2$), lower alkyl, lower alkenyl, lower alkynyl, lower alkoxy and a group of formula OCO—$R_7$ wherein $R_7$ is 2-furanyl, lower alkyl or lower alkoxy group, wherein all said radicals may optionally be substituted with a hydroxy, lower alkyl, lower alkenyl, lower alkynyl, lower alkoxy, amino, nitro, nitrile, carboxyl or haloalkyl radical; or
$R_2$ and $R_3$ may optionally form a cyclic structure of the formula:

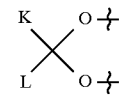

wherein, K and L are selected from the group consisting of hydrogen, and lower alkyl, or optionally K and L can form an alicyclic hydrocarbon or heterocyclic ring;
$R_4$ is hydrogen or halogen;
$R_5$ is hydrogen, hydroxyl, or oxygen;
P and Q are independently selected from the group consisting of hydrogen, chloro, fluoro and lower alkyl group;
X is oxygen or sulfur;
Y is methylene, oxygen or amino;
Z is oxygen or amino group; and
n is 1 to 4.

6. The compound as recited in claim 5 wherein;
$R_1$ is selected from the group consisting of hydrogen, hydroxyl, nitrite ester (ONO), nitrate ester ($ONO_2$), halogen, thiol, alkylmercapto group of 1 to 6 carbon atoms, heterocyclic group of 2 to 5 carbon atoms and 1 to 2 hetero atoms, lower alkoxy group of 1 to 6 carbon atoms, alkylsilyloxy group of 3 to 8 carbon atoms, and lower alkyl group of 1 to 6 carbon atoms, wherein all said radicals may optionally be substituted with a hydroxy, lower alkyl, lower alkenyl, lower alkynyl, lower alkoxy, amino, nitro, nitrite, carboxyl or haloalkyl radical; or
$R_1$ is a group of the formula OCO—$R_6$ wherein $R_6$ is an alkanoic acid group of 2 to 6 carbon atoms, lower alkyl group of 1 to 6 carbon atoms, lower alkenyl group of 2 to 6 carbon atoms, lower alkynyl group of 2 to 6 carbon atoms, or lower alkoxy group of 1 to 6 carbon atoms;
$R_2$ and $R_3$ are independently selected from the group consisting of hydrogen, hydroxyl, nitrite ester (ONO), nitrate ester ($ONO_2$), lower alkyl group of 1 to 6 carbon atoms, lower alkenyl group of 2 to 6 carbon atoms, lower alkynyl group of 2 to 6 carbon atoms, and lower alkoxy group of 1 to 6 carbon atoms, wherein all said radicals may optionally be substituted with a hydroxy, lower alkyl, lower alkenyl, lower alkynyl, lower alkoxy, amino, nitro, nitril, carboxyl and haloalkyl radical; or
$R_2$ and $R_3$ are a group of formula OCO—$R_7$ wherein $R_7$ is 2-furanyl, lower alkyl group of 1 to 6 carbon atoms or lower alkoxy group of 1 to 6 carbon atoms;
$R_2$ and $R_3$ may optionally form a cyclic structure of the formula:

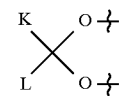

wherein, K and L are selected from the group consisting of hydrogen, and lower alkyl group of 1 to 6 carbon atoms;
optionally K and L can form an alicyclic hydrocarbon ring preferably containing a maximum of 8 carbon atoms or a heterocyclic ring preferably containing a maximum of 6 carbon atoms and 2 heteroatoms selected from nitrogen, oxygen or sulfur; and P and Q are independently selected from the group consisting of hydrogen, chloro, fluoro and lower alkyl group of 1 to 6 carbon atoms.

7. A compound having the formula:

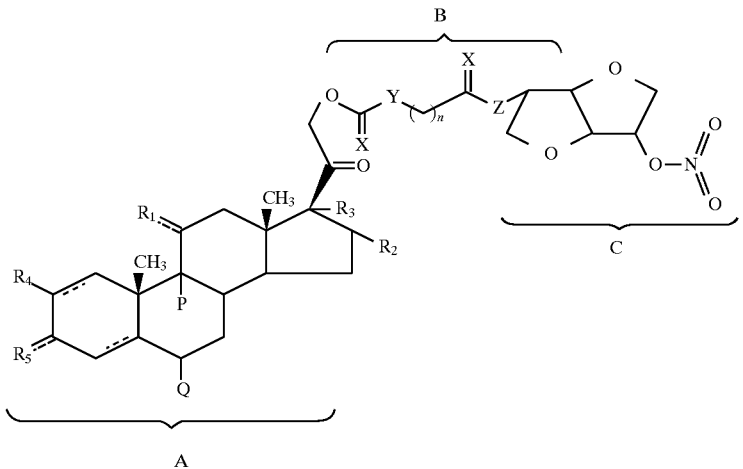

III and wherein;

the dotted line in Formula III indicates a single or a double bond;

R₁ is selected from the group consisting of hydrogen, hydroxyl, nitrite ester (ONO), nitrate ester (ONO₂), oxygen (ketone), lower alkoxy, alkylsilyloxy, and lower alkyl, wherein all said radicals may optionally be substituted with a hydroxy, lower alkyl, lower alkenyl, lower alkynyl, lower alkoxy, amino, nitro or haloalkyl radical; a group of formula OCO—R₆ wherein R₆ is alkanoic acid, lower alkyl, lower alkenyl, lower alkynyl or lower alkoxy group;

R₂ and R₃ are independently selected from the group consisting of hydrogen, hydroxyl, nitrite ester (ONO), nitrate ester (ONO₂), lower alkyl, lower alkenyl, lower alkynyl, lower alkoxy and a group of the formula OCO—R₇ wherein R₇ is 2-furanyl, lower alkyl, lower alkenyl, lower alkynyl or lower alkoxy group, wherein all said radicals may optionally be substituted with hydroxy, lower alkyl, lower alkenyl, lower alkynyl, lower alkoxy, amino, nitro, nitrile, carboxyl and haloalkyl radicals; or R₂ and R₃ may optionally form a cyclic structure of the formula:

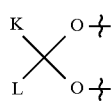

wherein, K and L are selected from the group consisting of hydrogen, and lower alkyl;

or optionally K and L can form an alicyclic hydrocarbon or heterocyclic ring

R₄ is hydrogen or halogen;

R₅ is hydrogen, hydroxyl or oxygen;

P and Q are independently selected from the group consisting of hydrogen, chloro, fluoro and lower alkyl;

X is oxygen or sulfur;

Y is methylene, oxygen or amino;

Z is oxygen or amino; and n is 1 to 4.

8. The compound as recited in claim 7 wherein:

R₁ is selected from the group consisting of hydrogen, hydroxyl, nitrite ester (ONO), nitrate ester (ONO₂), halogen, thiol, alkylmercapto group of 1 to 6 carbon atoms, heterocyclic group of 2 to 5 carbon atoms and 1 to 2 hetero atoms, lower alkoxy group of 1 to 6 carbon atoms, alkylsilyloxy group of 3 to 8 carbon atoms, and lower alkyl group of 1 to 6 carbon atoms, wherein all said radicals may optionally be substituted with a hydroxy, lower alkyl, lower alkenyl, lower alkynyl, lower alkoxy, amino, nitro, nitrile, carboxyl or haloalkyl radical; or R₁ is a group of the formula OCO—R₆ wherein R₆ is an alkanoic acid group of 2 to 6 carbon atoms, lower alkyl group of 1 to 6 carbon atoms, lower alkenyl group of 2 to 6 carbon atoms, lower alkynyl group of 2 to 6 carbon atoms, or lower alkoxy group of 1 to 6 carbon atoms;

R₂ and R₃ are independently selected from the group consisting of hydrogen, hydroxyl, nitrite ester (ONO), nitrate ester (ONO₂), lower alkyl group of 1 to 6 carbon atoms, lower alkenyl group of 2 to 6 carbon atoms, lower alkynyl group of 2 to 6 carbon atoms, and lower alkoxy group of 1 to 6 carbon atoms, wherein all said radicals may optionally be substituted with hydroxy, lower alkyl, lower alkenyl, lower alkynyl, lower alkoxy, amino, nitro, nitrile, carboxyl or haloalkyl radicals; or R₂ and R₃ are a group of formula OCO—R₇ wherein R₇ is 2-furanyl, lower alkyl group of 1 to 6 carbon atoms or lower alkoxy group of 1 to 6 carbon atoms;

R₂ and R₃ may optionally form a cyclic structure of the formula:

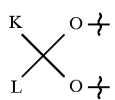

wherein, K and L are selected from the group consisting of hydrogen, and lower alkyl group of 1 to 6 carbon atoms;

optionally K and L can form an alicyclic hydrocarbon ring preferably containing a maximum of 8 carbon atoms or a heterocyclic ring preferably containing a maximum of 6 carbon atoms and 2 heteroatoms selected from nitrogen, oxygen or sulfur; and P and Q are independently selected from the group consisting of hydrogen, chloro, fluoro and lower alkyl group of 1 to 6 carbon atoms.

9. A pharmaceutical composition comprising a compound as recited in claim 1, 2, 3, 4, 5 or 6; and a pharmaceutically acceptable carrier.

10. A method of treating a patient with inflammation by administering a therapeutically effective amount of the compound as recited in claim 1, 2, 3, 4, 5 or 6.

11. The method of claim 10 wherein said patient also has undesired smooth muscle contractions.

* * * * *